United States Patent [19]

Takenaka et al.

[11] 4,308,406

[45] Dec. 29, 1981

[54] METHOD FOR PREVENTING THE DISCOLORATION OF DIHYDRIC PHENOLS

[75] Inventors: Masaaki Takenaka, Chiba; Haruhisa Harada, Ichihara; Hiroshi Maki, Ichihara; Shigeru Sasaki, Ichihara, all of Japan

[73] Assignee: Sumitomo Chemical Company Limited, Osaka, Japan

[21] Appl. No.: 152,391

[22] Filed: May 22, 1980

[30] Foreign Application Priority Data

Jun. 7, 1979 [JP] Japan .................................. 54-71876

[51] Int. Cl.$^3$ ........................ C07C 37/68; C07C 37/88
[52] U.S. Cl. .................................... 568/753; 568/742; 568/749; 568/763
[58] Field of Search ............... 568/753, 763, 749, 768, 568/742

[56] References Cited

U.S. PATENT DOCUMENTS

| | | | |
|---|---|---|---|
| 2,691,669 | 10/1954 | Walker | 568/749 |
| 2,736,753 | 2/1956 | Jacobs | 568/751 |
| 4,239,921 | 12/1980 | Hashimoto et al. | 568/753 |

FOREIGN PATENT DOCUMENTS

| | | | |
|---|---|---|---|
| 40-4813 | 3/1965 | Japan . | |
| 52-5717 | 1/1977 | Japan | 568/753 |
| 52-68134 | 6/1977 | Japan . | |

*Primary Examiner*—Werren B. Lone
*Attorney, Agent, or Firm*—Stevens, Davis, Miller & Mosher

[57] ABSTRACT

Dihydric phenol is effectively prevented from discoloration by mixing the dihydric phenol with 0.00001 to 0.1% by weight of hydrocarboxylic acid on the basis of the dihydric phenol.

7 Claims, No Drawings

METHOD FOR PREVENTING THE DISCOLORATION OF DIHYDRIC PHENOLS

The present invention relates to a method for preventing discoloration of dihydric phenols.

It is well known that dihydric phenols under storage acquire a color with the lapse of time due to the oxidation or the like, and also that the discoloration is more accelerated by contact with iron or the like. This discoloration results in a lowering in the commercial value of the phenols or disadvantages in use.

In order to prevent the discoloration of phenols, it is known to mix one phenols with a suitable additive, as disclosed in, for example, Published Unexamined Japanese Patent Application No. 68134/1977, wherein hydrazine or hydrazine hydrate is used as the additive. As for dihydric phenols, however, any effective additive has never been found.

The present inventors have earnestly studied a method for the prevention of dihydric phenols from discoloration, and found that the addition of a small amount of oxycarboxylic acids is remarkably effective in preventing discoloration of dihydric phenols under storage in solutions or solids, even though the phenols are in contact with iron pieces.

The present invention provides a method for preventing discoloration of a dihydric phenol represented by the formula,

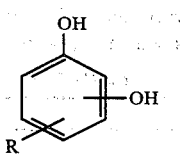

wherein R is a $C_1$–$C_6$ alkyl group or a hydrogen atom, which comprises mixing the dihydric phenol with a hydroxycarboxylic acid in an amount of 0.00001 to 0.1% by weight based on the weight of the dihydric phenol.

The dihydric phenols to be prevented from discoloration in accordance with the present invention include resorcinol, hydroquinone, catechol, 4-t-butylresorcinol, 4-n-hexylresorcinol and the like. Further, the dihydric phenols are not limited in their manufacturing methods, and include those which are produced, for example, by a so-called alkali fusion method and hydroperoxide method (refer to Mitsuaki Mukaiyama (Editor): Industrial Organic Chemistry published by Tokyo Chemical Group, 1978 French Pat. No. 1,319,454, U.S. Pat. No. 2,736,753). Moreover they can be used each alone or in a mixture of different kinds thereof.

The hydroxycarboxylic acids used in the present invention include for example tartaric acid, malic acid, lactic acid, tartronic acid and esters of these acids (e.g. methyl esters, ethyl esters, butyl esters). Of these, tartaric acid, malic acid and tartaric acid esters are particularly preferred.

The amount of the acid added depends generally upon storage conditions for the dihydric phenols, but generally it is within a range of 0.00001 to 0.1% by weight, particularly preferably 0.0001 to 0.05% by weight based on the weight of the dihydric phenol. Amounts below 0.00001% by weight have no effect to prevent discoloration, while amounts exceeding 0.1% by weight lower the purity of dihydric phenols to cause problems in terms of quality standards.

How to add the hydroxycarboxylic acid is not particularly limited. For example, a predetermined amount of the hydroxycarboxylic acid is added to the dihydric phenol, and the resulting mixture is heated at a temperature higher than the melting point of the dihydric phenol, but preferably lower than the temperature of the melting point plus 80° C. under an inert gas atmosphere (e.g. nitrogen gas atmosphere) or a reduced pressure for a period of time sufficient for obtaining a uniform mixture, usually for 1 to 5 hours. Thereafter, the melt is allowed to cool, and then formed into a desired form such as flakes. Alternatively, the mixing of the hydroxycarboxylic acid with the dihydric phenol may be carried out in an aqueous medium.

The acid may be added in solid powders or in aqueous solutions, each alone or in a mixture of two or more thereof.

The present invention will be illustrated in detail with reference to the following examples. Coloration was evaluated by yellowness index (hereinafter referred to as Y.I.) according to JIS K 7103.

EXAMPLE 1

Eight grams of resorcinol (produced by the hydroperoxide method) and 0.001% by weight of tartaric acid were added to a glass flask. The mixture was then melted, with and without addition of an iron piece (0.15 g; surface area, 2 cm$^2$), at 140° C. under reduced pressure and kept in the same state for 48 hours. The test was carried out in the same manner as above except that tartaric acid was not added. The melted resorcinol was formed into flakes, and Y.I. was measured by a photoelectric tristimulus colorimeter (produced by Nippon Denshoku Co.) to evaluate discoloration. The results are shown in Table 1. From the low Y.I. values of the systems containing tartaric acid, it is apparent that tartaric acid has a discoloration preventing effect.

TABLE 1

| Iron piece (in melted state) | Tartaric acid | Y.I. |
|---|---|---|
| Not added | Not added | 20–30 |
| " | 0.001% by weight | 7–8 |
| Added | Not added | 30 or more |
| " | 0.001% by weight | 13–14 |

Observed colors corresponding to Y.I. values are as follows:

| Y.I. Value | Observed color |
|---|---|
| 0–5 | Pure white without individual difference |
| 5–10 | White with a little individual difference |
| 10–15 | White giving a little yellowish impression |
| 15–20 | Pale yellow |
| 20–30 | Deep yellow (a reddish shade develops) |
| More than 30 | Yellowish brown (a reddish shade becomes stronger) |

EXAMPLE 2

To resorcinol obtained by the hydroperoxide method was added tartaric acid of varying amounts (0.00001, 0.0001, 0.001, 0.01, 0.05% by weight). In the same manner as in Example 1, each mixture was kept in the melted state at 140° C. for 48 hours, and Y.I. was measured and compared with the case wherein tartaric acid was not added. The results are shown in Table 2.

TABLE 2

| Dosage of tartaric acid (weight %) | Y.I. |
|---|---|
| 0 | 20–30 |
| 0.00001 | 10–15 |
| 0.0001 | 7–8 |
| 0.001 | 7–8 |
| 0.01 | 8–9 |
| 0.05 | 9–10 |

The Y.I. value of tartaric acid-containing resorcinol is lower in each case than that of resorcinol containing no tartaric acid, and it is apparent from the results that tartaric acid has a discoloration preventing effect. A particularly preferred range of the amount of tartaric acid was 0.0001 to 0.05% by weight. The same was observed with other oxycarboxylic acids such as malic acid and diethyl tartarate.

EXAMPLE 3

To resorcinol obtained by the hydroperoxide method, which was kept melted at 140° C., was added 0.001% by weight of tartaric acid, and then the resorcinol was formed into flakes. Similarly, flakes containing no tartaric acid were prepared as a reference. Both flakes were allowed to stand in a room, and the degree of coloration with the lapse of time was compared. Discoloration was evaluated in the same manner as in Example 1. Table 3 shows the change of Y.I. value with the lapse of time.

TABLE 3

| | Y.I. Standing period (day) | | | |
|---|---|---|---|---|
| Additive | 0 | 10 | 20 | 30 |
| No addition | 4 | 11 | 17 | 22 |
| Tartaric acid (0.001% by weight) | 1.5 | 4 | 6 | 6.5 |

It is apparent from the table that tartaric acid has a remarkable function to prevent discoloration of resorcinol in a solidified state.

EXAMPLE 4

To resorcinol obtained by the alkali fusion method, which was kept melted at 140° C., was added 0.001% by weight of tartaric acid, and then the resorcinol was formed into flakes. Similarly, flakes containing no tartaric acid were prepared as a reference. Both flakes were allowed to stand in a room, and the degree of discoloration with the lapse of time was compared. Discoloration was evaluated in the same manner as in Example 1. Table 4 shows the change of Y.I. value with the lapse of time.

TABLE 4

| | Y.I. Standing period (day) | | | |
|---|---|---|---|---|
| Additive | 0 | 10 | 20 | 30 |
| No addition | 2 | 7 | 10 | 13 |
| Tartaric acid (0.001% by weight) | 1 | 2.5 | 3.5 | 4 |

It is apparent from Table 4 that tartaric acid has also a function to prevent discoloration of resorcinol produced by the alkali fusion method.

EXAMPLE 5

Catechol (8 g) and 0.001% by weight of tartaric acid were added to a glass ampoule, melted at 140° C. under reduced pressure and then kept in the same condition for 72 hours. After the catechol was cooled and solidified (formed into flakes), the degree of discoloration of the catechol was compared with that of a reference catechol containing no tartaric acid. Evaluation was made in the same manner as in Example 1. The results are shown in Table 5.

TABLE 5

| Additive | Y.I. |
|---|---|
| No addition | 15–20 |
| Tartaric acid (0.001% by weight) | 6–7 |

It is apparent that tartaric acid has a discoloration preventing effect. The same results were obtained with other oxycarboxylic acids such as malic acid and diethyl tartarate.

EXAMPLE 6

To resorcinol produced by the hydroperoxide method was added 0.001% by weight of each of malic acid and diethyl tartarate. In the same manner as in Example 1, an iron piece was added and each mixture was kept in a melted state at 140° C. for 48 hours. After cooling and solidifying, the Y.I. value of the solidified resorcinol was compared with that of resorcinol alone. The results are shown in Table 6.

TABLE 6

| Additive | Y.I. |
|---|---|
| No addition | 30 or more |
| Malic acid | 13–14 |
| Diethyl tartarate | 13–14 |

EXAMPLE 7

To resorcinol produced by the hydroperoxide method, which was kept in a melted state at 140° C., was added 0.001% by weight of malic acid, and then the resorcinol was formed into flakes. The flakes were allowed to stand in a room, and the degree of discoloration with the lapse of time was examined. The evaluation of discoloration was made in the same manner as in Example 1. The results are shown in Table 7.

TABLE 7

| | Y.I. Standing period (day) | | | |
|---|---|---|---|---|
| Additive | 0 | 10 | 20 | 30 |
| No addition | 4 | 11 | 17 | 22 |
| Malic acid (0.001% by weight) | 2 | 4.5 | 6 | 7 |

EXAMPLE 8

An aqueous solution containing 5 g/100 ml of hydroquinone and a mixture of the aqueous solution and 0.05% by weight of tartaric acid were left as they were at room temperature for 48 hours. The test liquors were each placed in a cell and measured for Y.I. to compare the degree of discoloration. The results are shown in Table 8. The test liquor containing tartaric acid has a lower Y.I., which means that tartaric acid has also a discoloration preventing effect on hydroquinone. The same results were obtained with other oxycarboxylic acids.

TABLE 8

| Additive | Y.I. |
| --- | --- |
| No addition | 10-15 |
| Tartaric acid (0.05% by weight) | 2-5 |

EXAMPLE 9

Hydroquinone purified by sublimation (8 g) and a mixture of the hydroquinone (8 g) and 0.01% by weight of tartaric acid were each melted at 180° C. for 2 hours under reduced pressure. After cooling and solidifying, the test samples were measured for Y.I. The results are shown in Table 9.

TABLE 9

| Additive | Y.I. |
| --- | --- |
| No addition | 50 or more |
| Tartaric acid (0.01% by weight) | 20-30 |

The test sample containing no tartaric acid turned brown (a little reddish-brown). Even the test sample containing tartaric acid has a larger Y.I. than resorcinol, but the discoloration preventing effect of tartaric acid is clearly observed.

EXAMPLE 10

Test samples were prepared by adding hydroquinone of varying amounts (0.5%, 1%) and tartaric acid (0.001% by weight) to resorcinol. In the same manner as in Example 1, the samples were each melted at 140° C. and cooled to solidify. The solidified samples were then allowed to stand in a room, and the change of Y.I. with the lapse of time was measured. The results are shown in Table 10.

TABLE 10

| Condition (additive) | | Y.I. Standing period (day) | | | |
| --- | --- | --- | --- | --- | --- |
| | | 0 | 10 | 20 | 30 |
| Hydroquinone | 1.0% | 5.5 | 17 | 25 | 32 |
| Hydroquinone Tartaric acid | 1.0% 0.001% by weight | 1 | 2.5 | 3.5 | 4 |
| Hydroquinone Hydroquinone Tartaric acid | 0.5% 0.5% 0.001% by weight | 4 1 | 12 2.5 | 17 3.5 | 22 4 |
| Hydroquinone Hydroquinone Tartaric acid | not added not added 0.001% by weight | 1.5 1 | 7 2.5 | 10 3.5 | 12 4 |

As shown in Example 9, hydroquinone colors so strongly that strong coloration by the addition of a small amount of hydroquinone is observed as apparent from Table 10. It is however clear that the test samples containing tartaric acid are prevented from discoloration owing to hydroquinone.

What is claimed is:

1. A method of substantially preventing discoloration of a dihydric phenol represented by the general formula,

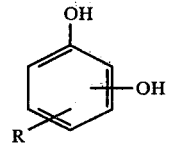

wherein R is a hydrogen atom or an alkyl group having 1-6 carbon atoms, comprising mixing the dihydric phenol with a hydroxycarboxylic acid in an amount of 0.00001 to 0.1% by weight based on the weight of the dihydric phenol, said acid being selected from the group consisting of tartaric acid, malic acid, lactic acid, tartronic acid and esters of said acids.

2. The method according to claim 1, wherein the hydroxycarboxylic acid is at least one member selected from tartaric acid, tartronic acid and esters thereof.

3. The method according to claim 1, wherein the mixing is effected at a temperature higher than the melting point of the dihydric phenol.

4. The method according to claim 3, wherein the mixing is effected under atmospheric or a reduced pressure.

5. The method according to claim 1, wherein the mixing is effected in an aqueous medium.

6. A dihydric phenol substantially prevented from discoloration by the method of claim 1.

7. The method of claim 1, wherein said phenol is resorcinol.

* * * * *